United States Patent [19]

Studer et al.

[11] Patent Number: 5,284,878
[45] Date of Patent: Feb. 8, 1994

[54] LIQUID PHASE METHANOL PROCESS WITH CO-RICH RECYCLE

[75] Inventors: David W. Studer, Wescosville; Elizabeth S. Schaub, Allentown, both of Pa.

[73] Assignee: Air Products and Chemicals, Inc., Allentown, Pa.

[21] Appl. No.: 49,238

[22] Filed: Apr. 16, 1993

Related U.S. Application Data

[63] Continuation of Ser. No. 831,150, Feb. 4, 1992, abandoned.

[51] Int. Cl.$^5$ .............................................. C07L 27/06
[52] U.S. Cl. ................................ 518/700; 60/39.12; 60/39.02; 429/12; 48/197 R; 48/197 FM
[58] Field of Search ...................... 518/700; 60/39.12; 429/12; 48/197 R, 197 FM

[56] References Cited

U.S. PATENT DOCUMENTS

| | | | |
|---|---|---|---|
| 4,031,123 | 6/1977 | Espino et al. | 260/449.5 |
| 4,567,204 | 1/1986 | Mednick et al. | 518/700 |
| 4,766,154 | 8/1988 | Bonnell et al. | 518/700 |
| 4,946,477 | 8/1990 | Perka et al. | 48/197 |

OTHER PUBLICATIONS

Roberts, et al; "The Liquid Phase Methanol Process–an Efficient Route to Methanol from Coal"; Apr. 1985.
Studer, et al; "Status Report on the Liquid Phase Methanol Project"; May 1990; pp. 16-1 et seq.
Chem Systems, Inc; "Optimization of Electricity-Methanol Production"; Jun. 1990.
Sherwin, et al; "Liquid Phase Methanol"; May 1978; p. 2-2.
"Slurry Reactor Design Studies: Slurry vs. Fixed-Bed Reactors for Fischer-Tropsch and Methanol"; (Jun. 1990) p. 24.
Walters, et al; "Methanol Coproduction with a Baseload IGCC Plant"; Oct. (1990); pp. 3–4 and Slide #8.
Sherwin, et al; "Liquid Phase Methanol"; Dec. (1979); pp. 3–7.

*Primary Examiner*—Howard T. Mars
*Attorney, Agent, or Firm*—John M. Fernbacher; James C. Simmons; William F. Marsh

[57] ABSTRACT

Methanol is produced by reacting a CO-rich synthesis gas in the presence of a powdered methanol synthesis catalyst suspended in an inert liquid in a liquid phase reactor system. Unreacted CO-rich synthesis gas is recycled to the reactor, thus increasing methanol production and reducing specific power compared with once-through operation without recycle or compared with recycle of hydrogen-rich gas recovered from unreacted synthesis gas. The process preferably is integrated with a coal gasification electric power generation system in which a portion of the unreacted synthesis gas is used as power generation fuel and a portion of the methanol product is used as additional power generation fuel during periods of peak power demand.

9 Claims, 3 Drawing Sheets

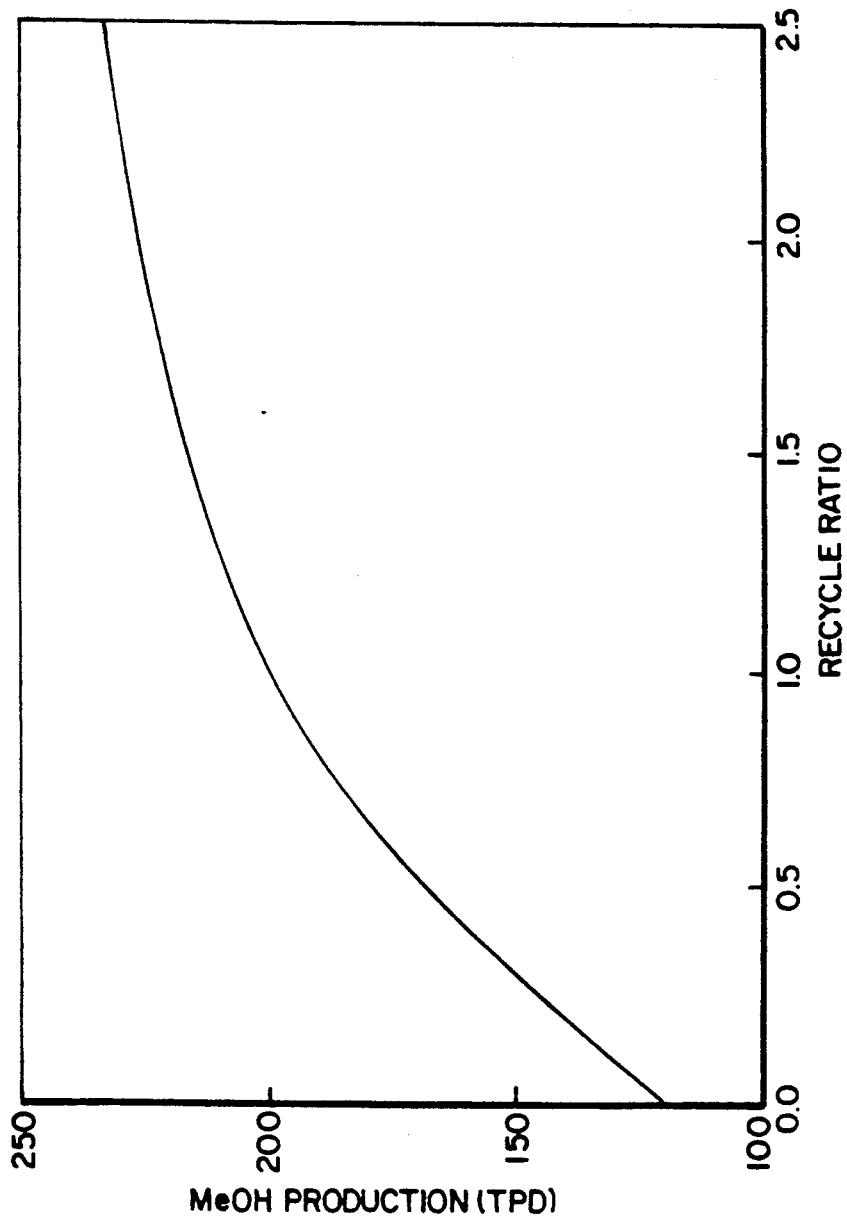

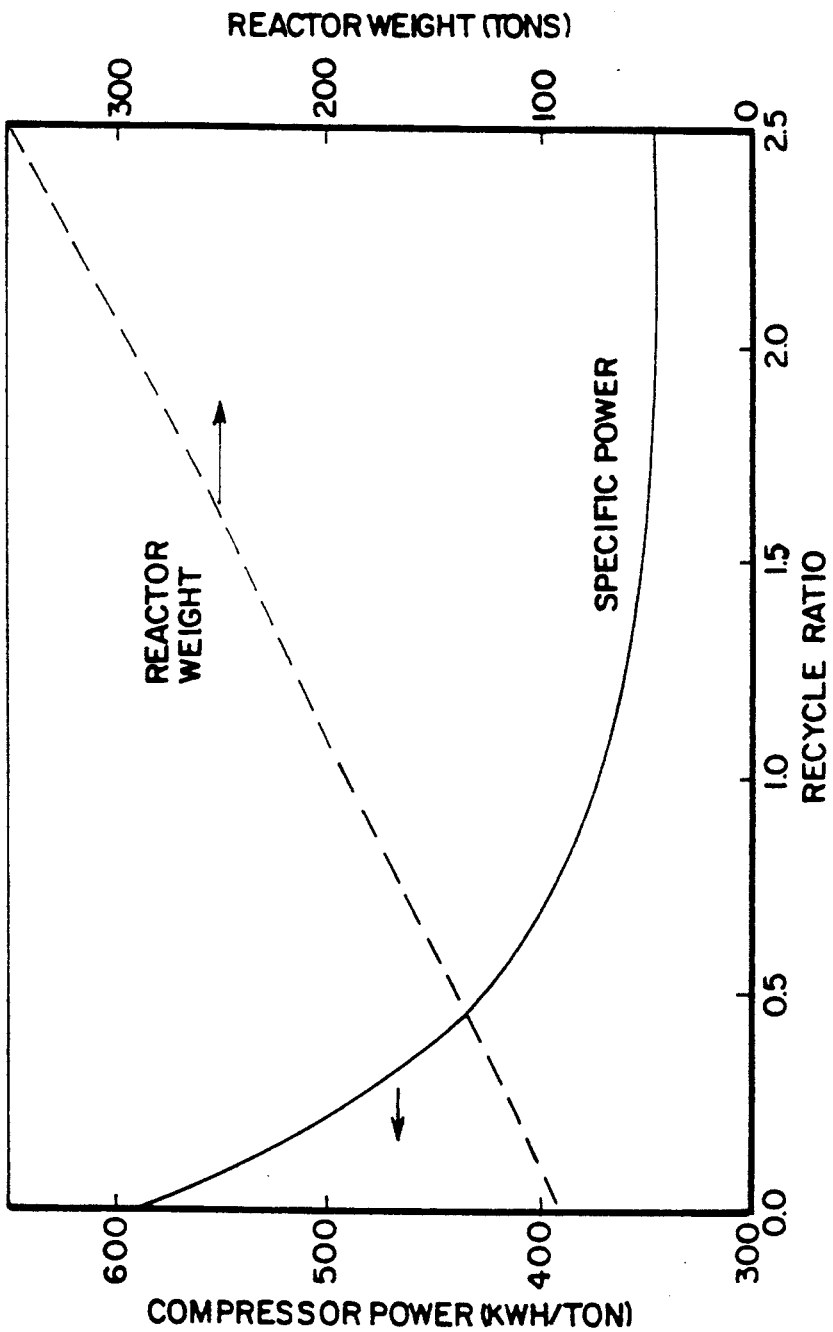

LIQUID PHASE METHANOL PROCESS WITH CO-RICH RECYCLE

This is a continuation of copending application Ser. No. 07/831,150 filed on Feb. 4, 1992 now abandoned.

FIELD OF THE INVENTION

The invention pertains to a method for producing methanol from synthesis gas in a liquid phase reactor system, and in particular to the operation of a liquid phase reactor system which utilizes a CO-rich synthesis gas feed to produce methanol and fuel gas.

BACKGROUND OF THE INVENTION

Methanol is produced commercially from hydrogen-rich synthesis gas in a packed bed catalytic reactor operated in the gas phase with means for removing heat from the highly exothermic methanol synthesis reaction. Synthesis gas is shifted when necessary so that the reactor feed is hydrogen-rich and dilute in carbon oxides, typically containing carbon monoxide concentrations no greater than 6 to 9 vol%. Hydrogen-rich unreacted synthesis gas is recycled back to the reactor in order to moderate the reactor temperatures and increase the overall conversion to methanol. Unreacted synthesis gas is enriched in hydrogen prior to recycle in certain cases when more unreacted synthesis gas is produced than is needed for the plant fuel system.

Methanol synthesis alternately can be accomplished in a liquid phase reactor system in which synthesis gas is reacted in the presence of a powdered catalyst suspended in an inert liquid, which allows much higher per pass conversion and more effective removal of reaction heat and control of catalyst temperature compared with a gas-phase reactor system. The liquid phase methanol process is described in detail in U.S. Pat. No. 4,031,123 and 4,567,204, the specifications of which are incorporated herein by reference.

The liquid phase methanol (LPMEOH) process can be operated in different modes depending on specific applications. An article by G. W. Roberts et al entitled "The Liquid Phase Methanol Process—an Efficient Route to Methanol from Coal" presented at the Conference on Coal Gasification and Synthetic Fuels for Power Generation, San Francisco, 14–18 April 1985, describes the operation of the LPMEOH process on a once-through basis using unshifted, CO-rich synthesis gas in which the process is integrated with a coal gasifier in a coal gasification combined cycle (CGCC) power generation system. Unconverted synthesis gas is utilized as gas turbine fuel and methanol is stored for use as gas turbine fuel during peak power demand. The LPMEOH process also can be operated in a standalone mode to maximize methanol production. In this case, if CO-rich synthesis gas feed is utilized, the gas must be shifted prior to the reactor to yield the required 2:1 stoichiometric $H_2/CO$ molar ratio for methanol synthesis, and unconverted gas is recycled directly to the reactor to increase overall methanol yield. Further descriptions of once-through LPMEOH systems are given by Studer et al in a paper entitled "Status Report on the Liquid Phase Methanol Project" published in the Proceedings of the 14th Annual EPRI Conference on Fuel Science, GS-6827, May, 1990, p. 16-1 et seq. and in a report by Chem Systems, Inc. entitled "Optimization of Electricity-Methanol Production", Final Report, GS-6869, prepared for the Electric Power Research Institute, June, 1990.

The operation of a LPMEOH reactor system with recycle of unreacted gas to achieve high conversion requires a stoichiometric feed, as pointed out in a report by the Bechtel Group entitled "Slurry Reactor Design Studies: Slurry vs Fixed-Bed Reactors for Fischer-Tropsch and Methanol", Final Report to the U. S. Department of Energy, DOE/PC/89867-T2, June 1990 at p. 24; the unreacted synthesis gas is recycled directly to the reactor as shown in FIG. E-1 at p. 188. This requirement for stoichiometric or shifted feed gas for the operation of LPMEOH reactors in the recycle mode is also described in a report by A. B. Walters and S. S. Tam entitled "Methanol Coproduction with a Baseload IGCC Plant", 9th EPRI Conference on Coal Gasification Power Plants, Palo Alto, Calif., October 1990, at pp. 3–4 and Slide #8. Further discussion of this requirement is given by M. Sherwin and D. Blum in their report entitled "Liquid Phase Methanol", AF-1291, Final Report to the Electric Power Research Institute, December 1979, at p. 3-7. Koppers-Totzek synthesis gas is CO-rich as shown in Table 3—3 at p. 3-5.

An alternate method for the operation of a LPMEOH reactor with recycle is described in U.S. Pat. No. 4,946,477 in which the reactor is fed with CO-rich synthesis gas, the unreacted synthesis gas is separated into a hydrogen-rich stream and a CO-rich stream, and the hydrogen-rich stream is recycled to the reactor feed (FIG. 7). Alternately, water can be added to the synthesis gas feed to promote CO shift within the LPMEOH reactor (FIG. 8). Addition of water to a CO-rich synthesis gas feed is also discussed by M. Sherwin and D. Blum in a report entitled "Liquid Phase Methanol", AF-693, Interim Report to the Electric Power Research Institute, May 1978, at p. 2—2. It is stated that a hydrogen-rich unconverted reactor effluent gas can be obtained by water addition to a CO-rich synthesis gas feed, and that water co-feeding may be of interest where total conversion to methanol is required and the reactor effluent gas is recycled.

U.S. Pat. No. 4,766,154 discloses a two-stage LPMEOH reactor system operated in series using hydrogen-rich synthesis gas feed. Unreacted synthesis gas from the first stage passes to the second stage reactor, and unreacted synthesis gas from the second stage reactor is recycled to the second stage reactor feed. The synthesis gas feed, unreacted synthesis gas from the first stage reactor, and unreacted synthesis gas from the second stage reactor are all hydrogen-rich streams as given in Table I.

The operation of a LPMEOH reactor using stoichiometric or hydrogen-rich synthesis gas feed yields a stoichiometric or hydrogen-rich reactor effluent stream as is known in the art. When such a LPMEOH reactor is operated in the recycle mode, the recycle stream is thus hydrogen-rich. As noted above, a LPMEOH reactor operating with a CO-rich synthesis gas feed with water addition can produce a hydrogen-rich effluent gas, which is favored for recycle operation when total syngas conversion to methanol is desired. The operation of LPMEOH reactors in the recycle mode as disclosed in the prior art described above thus involves exclusively the recycle of stoichiometric or hydrogen-rich streams to the reactor feed.

SUMMARY OF THE INVENTION

The present invention is a method for producing methanol and fuel gas from a CO-rich synthesis gas feed in a liquid phase reactor containing a methanol synthesis catalyst suspended in an inert liquid, wherein a portion of the CO-rich unreacted synthesis gas is recycled directly to the reactor feed. This recycle operation increases methanol production and reduces the specific power required for methanol production; the preferred ratio of recycle to fresh feed is between about 0.1 and 2.0. The LPMEOH reactor optionally can be integrated with a coal gasification electric power generation system for the cogeneration of methanol and electric power.

BRIEF DESCRIPTION OF THE DRAWINGS

FIG. 2 is a plot of methanol production vs recycle ratio according to the present invention.

FIG. 3 is a plot showing the effect of recycle ratio on the specific compressor power and the weight of the methanol reactor according to the present invention.

DETAILED DESCRIPTION OF THE INVENTION

Figure 1:
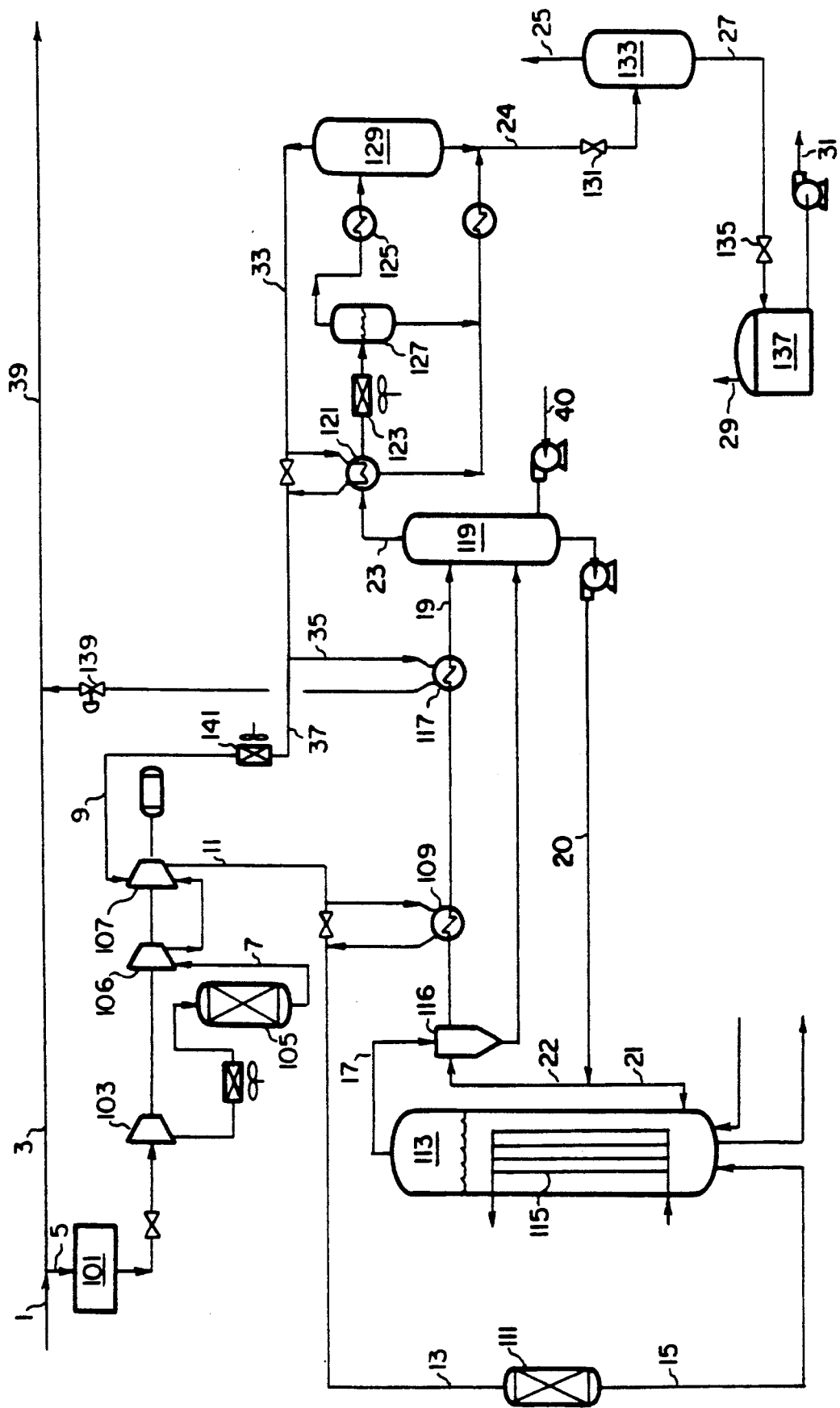
FIG. 1 is a process flow diagram of a liquid phase methanol system illustrating the method of the present invention.

The present invention is a method for producing methanol and fuel gas by reacting a CO-rich synthesis gas in the presence of methanol synthesis catalyst suspended in an inert liquid wherein a portion of the CO-rich unreacted synthesis gas is recycled to the reactor. This recycle step allows higher methanol production and reduces the specific power for methanol production. In contrast with the prior art teachings regarding operation of LPMEOH reactors in a recycle mode, in which the recycled gas is always stoichiometric or hydrogen-rich, the present invention teaches the use of a CO-rich fresh synthesis gas feed and the recycle of the resulting CO-rich unreacted synthesis gas directly to the reactor. This recycle of CO-rich gas to a reactor which utilizes a CO-rich fresh feed is unconventional and unique because it changes the total reactor feed composition (fresh feed plus recycle) further from the stoichiometric $H_2/CO$ ratio of 2, rather than subjecting the reactor feed to the water-gas shift reaction and/or treating the recycled gas in order to change the total reactor feed composition towards the stoichiometric ratio of 2 as taught in the prior art.

The term CO-rich is used in the present specification to define a synthesis gas which contains a concentration of carbon monoxide in excess of that required for stoichiometric reaction with the hydrogen in the synthesis gas to produce methanol. The term hydrogen-rich is used to define a synthesis gas which contains a concentration of hydrogen in excess of that required for stoichiometric reaction with the carbon monoxide in the synthesis gas to make methanol. Thus a synthesis gas having a molar $H_2/CO$ ratio greater than 2 is hydrogen-rich and less than 2 is CO-rich. Since $CO_2$ if present in the synthesis gas also reacts with hydrogen to produce methanol, synthesis gas alternately may be characterized by the molar ratio $(H_2-CO_2)/(CO+CO_2)$. In the present invention, this $(H_2-CO_2)/(CO+CO_2)$ ratio is preferably between about 0.3 and 2.0 for fresh synthesis gas feed and between about 0.1 and 2.0 for unreacted synthesis gas.

It has been found that recycling CO-rich unreacted synthesis gas in a LPMeOH reactor operating on CO-rich fresh feed increases the methanol production rate and decreases the specific power required for methanol production. This result is realized chiefly because the power consumption required to enrich the recycle stream in hydrogen, which would be required based on the prior art described above, is not required in the present invention. Further, the unreacted synthesis gas pressure is closer to the reactor feed pressure, having been subjected only to the reactor pressure drop (typically in the range of 50 to 150 psi), and thus requires minimal recompression to be combined with the fresh synthesis gas feed for further reaction. This reduction in specific power is especially attractive in locations where electric power is expensive, and also allows the efficient coproduction of methanol when the LPMEOH system is integrated with a coal gasification electric power generation system. This power reduction is offset, however, by an increase in the size of the methanol reactor required for the increased gas flow at the same space velocity. As will be illustrated in the Examples, there is an optimum range of recycle ratios in which the tradeoff between power cost and reactor capital cost results in a minimum overall methanol product cost. It has been found that this preferred range is defined by a recycle ratio (recycle molar flow divided by fresh feed molar flow) between about 0.1 and 2.0; the incremental benefits of increased recycle begin to diminish as the recycle ratio is increased above about 1.0. The actual optimum recycle ratio will depend upon relative capital costs and power costs, and thus will vary according to plant location. The optimum recycle ratio also may depend upon the degree of integration of the LPMEOH reactor system with a coal gasification electric power generation system.

The coal gasification system can utilize any coal gasification process which provides a satisfactory synthesis gas useful as fuel gas for power generation. Commercial coal gasification processes offered by Shell, Texaco, and Dow are preferred processes to generate such fuel gas. This fuel gas can be used to fire gas turbines in a coal gasification combined cycle (CGCC) power generation system in which coal gasification and power generation are integrated into a single power generation system. Methanol production by the process of the present invention can be integrated with the CGCC system. Alternately, the fuel gas may be utilized in fuel cells in which hydrogen and CO undergo electrochemical oxidation to produce electric power directly as is known in the art. The coal gasification, methanol production by the process of the present invention, and fuel cell system can be integrated into a single power generation system.

A process flow diagram illustrating the method of the present invention is given in FIG. 1. CO-rich synthesis gas stream 1, produced for example by a Texaco or Shell coal gasification process, previously treated to remove entrained contaminants and optionally a portion of the sulfur compounds contained therein, is divided into fuel gas stream 3 and raw LPMeOH feed stream 5. Feed stream 5 is further treated if required in acid gas removal system 101 as is known in the art to remove hydrogen sulfide, carbonyl sulfide, hydrogen cyanide, and optionally carbon dioxide, is compressed in first stage compressor 103, and optionally is treated to remove iron and nickel carbonyl compounds in adsorbent guard bed 105. Contaminant-free synthesis gas 7 is compressed in second stage compressor 106, combined with recycle stream 9 and further compressed in third stage compressor 107 to reactor feed gas stream 11 at a pressure of 500 to 1500 psig. This stream is optionally preheated in exchanger 109 against reactor product gas, heated feed stream 13 passes through guard bed 111 for final sulfur removal, and final feed stream 15 flows into liquid phase methanol reactor 113. Methanol synthesis catalyst in powdered form is suspended in an inert liquid in reactor 113, typically at concentrations between about 25 and 50 wt%. Any methanol synthesis catalyst can be used; the well-known commercially-available catalyst comprising copper and zinc on alumina is satisfactory for this process. The inert liquid can be selected from a wide range of materials including hydrocarbon oils, oxygenated liquids, and the like. The liquid must be inert with respect to reaction with synthesis gas components as well as the catalyst. The vapor pressure of the liquid should be low enough to allow reasonable control of vaporized liquid losses from the reactor. Useful liquids for such service include paraffinic oils such as Freezene 100 and Witco 40, both made by Witco, and paraffinic-naphthenic oils such as Drakeol 7 and Drakeol 10 made by Penreco. Most of the exothermic heat of reaction is removed by heat exchanger 115, typically by converting boiler feedwater to steam, to control the temperature in reactor 113 between about 440° F. and 600° F., preferably between about 465° F. and 500° F. The reactor is typically operated at pressures between about 500 and 1500 psig. Reactor effluent stream 17, containing methanol and unconverted synthesis gas which is always richer in CO than the CO-rich synthesis gas feed, passes through entrained catalyst cyclone 116, optionally is cooled against reactor feed, and is further cooled by exchange with unreacted synthesis gas in exchanger 117.

Cooled raw product stream 19 passes into separator 119 where condensed process liquid components and entrained catalyst are recovered. Liquid stream 20 from separator 119 consists of fresh makeup oil 40, entrained catalyst and condensed process liquid 19, and entrained catalyst and process liquid from cyclone 116. A portion 21 of stream 20 is returned to LPMEOH reactor 113 and the remainder 22 is returned to cyclone 116. Methanol and unreacted synthesis gas stream 23 is cooled in coolers 121, 123, and 125, and condensed methanol streams from cooler 121, separator 127, and separator 129 are combined into methanol stream 24. Methanol stream 24 is flashed across valve 131 and passed into separator 133, from which fuel gas stream 25 and methanol stream 27 are withdrawn. Methanol stream 27 is further reduced in pressure across valve 135 and held in final methanol product tank 137. Additional fuel gas 29 is withdrawn from tank 137. Methanol product stream 31 is withdrawn as required and may be used as additional fuel for increased electric power generation during peak demand periods; alternately a portion of the methanol may be utilized as a separate chemical or fuel product.

CO-rich unreacted synthesis gas stream 33 is withdrawn from separator 129, heated in exchanger 121, and divided into streams 35 and 37. Purge stream 35 is heated in exchanger 117, throttled across valve 139, and combined with synthesis gas stream 3 into fuel gas stream 39 which can be used as fuel to fire gas turbines in a coal gasification combined cycle power generation plant. Alternately, the fuel gas may be utilized in fuel cells in which hydrogen and CO undergo electrochemical oxidation to produce electric power directly. CO-rich unreacted synthesis gas stream 37 is cooled in cooler 141 and becomes LPMEOH reactor recycle stream 9. Since the pressure of recycle stream 9 is lower than synthesis gas feed stream 11 only by the pressure drop in the reactor system, stream 9 may be combined with partially-compressed fresh synthesis gas between stages of a multi-staged feed compressor. In FIG. 1 these streams are combined in the suction of final compressor stage 107.

The flow rates of streams 3, 5, 35, and 37 are determined by the required amount of methanol product and the desired recycle ratio for operation of the LPMEOH reactor system. Typically about 25 to 100%, of synthesis gas stream 1 is withdrawn as fresh feed 5 for the LPMEOH reactor system, and 10 to 30%, of unreacted synthesis gas stream 33 is withdrawn as purge stream 35. Preferably, the flow rate of stream 35 is limited to the amount required as purge to control the undesired buildup of specific components in the recycled gas.

EXAMPLE 1

A heat and material balance was prepared for the flowsheet of FIG. 1 using a reactor model based upon pilot plant data for reaction kinetics, heat transfer, and mass transfer in a liquid phase reactor operating on CO-rich synthesis gas. The feed gas for this Example was provided at 395 psia and contained 39.4 mol% $H_2$, 39.9 mol%. CO, 19.9 mol%, $CO_2$, 0.7 mol% $N_2$, and 0.1 mol%, methane. The reactor operating conditions were 1172 psia, 482° F., a feed rate of 4593 lbmol/hr, and a space velocity of 10,000 std liters/hr-kg. Catalyst activity was assumed to be 50% of fresh catalyst activity. The recycle ratio (recycle molar flow to fresh synthesis gas feed molar flow) was varied from 0 to 2.5, and the methanol production, compression power, specific compression power, and reactor size were calculated as summarized in Table 1.

TABLE 1

Effect of Recycle Ratio on Process Performance

| Recycle Ratio | Methanol Product, tons/day | Compr. Power, KW | Specific Power, KWH/ton | Reactor Diam., Ft. | Reactor Height, Ft. | Reactor Weight, tons |
| --- | --- | --- | --- | --- | --- | --- |
| 0.0 | 118 | 2910 | 593 | 5.7 | 39.8 | 90 |
| 0.5 | 169 | 3002 | 426 | 6.9 | 41.0 | 138 |
| 1.0 | 200 | 3094 | 371 | 8.0 | 42.1 | 191 |
| 1.5 | 217 | 3185 | 352 | 8.9 | 43.0 | 241 |
| 2.0 | 227 | 3277 | 346 | 9.7 | 43.8 | 293 |
| 2.5 | 234 | 3369 | 346 | 10.5 | 44.6 | 350 |

A plot of methanol production vs recycle ratio is given in FIG. 2 and plots of specific compression power and reactor weight vs recycle rate are given in FIG. 3. It can be seen that increasing the recycle ratio from 0.0 to 1.0 significantly increases the methanol production rate and reduces the specific power. Above a recycle ratio of about 1.0, however, increasing the recycle ratio has a diminishing impact on these two parameters. The total reactor weight, which is generally proportional to reactor capital cost, increases nearly linearly with recycle ratio. The optimum recycle ratio which yields minimum methanol cost will depend on upon relative capital costs and power costs, and thus will vary according to plant location. Typically, the preferred recycle ratio which minimizes methanol cost will fall in the range of about 0.5 to 1.5.

EXAMPLE 2

Two additional heat and material balances were prepared using the conditions of Example 1 for comparison with a once-through liquid phase methanol reactor (Case 1—recycle ratio of 0.0 in Table 1) and a preferred CO-rich recycle case (Case 4—recycle ratio of 1.0 in Table 1). The first of these additional balances, Case 2, was prepared at the same process conditions as the once-through case except that the reactor was operated at a higher pressure of 1472 psia. The second additional balance, Case 3, was prepared at the same process conditions as the CO-rich recycle case except that the unreacted synthesis gas was separated into a hydrogen-rich stream and a more CO-rich stream using a membrane separator, and the hydrogen-rich stream was compressed and recycled to the reactor. A summary of the conditions and calculated reactor performance is given in Table 2.

tion rate and results in a significant decrease in specific power compared with Cases 1-3. Each of the Cases 2-4 offers improvements over the base Case 1 at the expense of additional capital cost. Case 2 requires an increase in compressor operating pressure and a reactor with a higher pressure rating; Case 3 requires a membrane separation module and an additional complete compressor; Case 4 requires an increase in compression capacity at a relatively small compression ratio (to compensate for reactor pressure drop) and a larger reactor. The present invention as illustrated by Case 4 thus allows a significantly larger increase in methanol production rate and decrease in specific power over the base Case 1 than realized in Cases 2 and 3, and these significant improvements are unexpected in view of the apparent kinetic and thermodynamic disadvantages of recycling CO-rich gas to the reactor feed.

The present invention thus provides a new method for increasing methanol production and decreasing the specific power required for this production in a liquid phase reaction system operating with a CO-rich synthesis gas feed, and is particularly useful when the reaction system is integrated with a coal gasification electric power generation system. The key feature of the invention, which is the recycling of CO-rich unreacted synthesis gas to the CO-rich reactor feed, differs markedly from prior art teaching wherein recycled gas is always stoichiometric or hydrogen-rich regardless of the fresh synthesis gas feed composition. The improvements real-

TABLE 2

Process Performance for Alternate Reactor Operating Conditions

|  | Case 1 Once-Through | Case 2 Once-Through | Case 3 Hydrogen-Rich Recycle | Case 4 CO-Rich Recycle |
|---|---|---|---|---|
| Reactor Feed |  |  |  |  |
| Pressure, psia | 1172 | 1472 | 1172 | 1172 |
| $H_2/CO$ molar ratio | 0.99 | 0.99 | 1.26 | 0.74 |
| $(H_2 - CO_2)/CO + CO_2)$ | 0.33 | 0.33 | 0.37 | 0.11 |
| Reactor Performance |  |  |  |  |
| Productivity, gmol/hr-kg | 33.0 | 40.4 | 33.6 | 26.9 |
| CO conversion, % per pass | 17.9 | 22.1 | 20.9 | 13.7 |
| MeOH Production, tons/day | 118 | 148 | 154 | 200 |
| Compression Power, KW | 2910 | 3292 | 3556 | 3094 |
| Specific Power, KWH/ton MeOH | 593 | 592 | 555 | 371 |

The results of Table 2 show that an increase in reactor pressure (Case 2) and the use of hydrogen recycle (Case 3) both improve reactor performance over the base case (Case 1). As would be expected, the changes in Cases 2 and 3 improve the methanol reaction kinetics and equilibrium as reflected in higher reactor productivity, CO conversion, and methanol production rate compared with Case 1. The specific power is also reduced by about 6% in Case 3. The direct recycle of CO-rich unreached synthesis gas as illustrated in Case 4, which is the key feature of the present invention, would be expected to degrade both the reaction kinetics and the equilibrium conversion because this recycle moves the total reactor feed composition further from the stoichiometric $H_2/CO$ molar ratio of 2. This in fact occurs, as seen in the decrease of reactor productivity and CO conversion per pass for Case 4 compared with Cases 1-3. In spite of these unfavorable changes, however, the recycle of CO-rich unreacted synthesis gas of Case 4 allows an increase in overall methanol producized from the present invention are unexpected in view of the conventional practice of recycling gas with compositions which move the combined recycle and fresh feed stream compositions closer to the stoichiometric $H_2/CO$ molar ratio of 2.0.

The essential characteristics of the present invention are described completely in the foregoing disclosure. One skilled in the art can understand the invention and make various modifications thereto without departing from the basic spirit thereof, and without departing from the scope and range of equivalents of the claims which follow.

We claim:

1. A method for the production of methanol and fuel gas comprising:
    (a) reacting hydrogen and carbon oxides at an elevated pressure in a liquid phase reactor system in the presence of a methanol synthesis catalyst suspended in an inert liquid to yield methanol and unreacted synthesis gas, wherein said hydrogen and carbon oxides are supplied in a reactor feed synthesis gas comprising fresh feed synthesis gas and recycled synthesis gas; and (b) separating said methanol from said unreacted synthesis gas, and dividing said unreacted synthesis gas into a fuel gas product and said recycled synthesis gas;

wherein each of said reactor feed synthesis gas, fresh feed synthesis gas, and recycled synthesis gas has a molar ratio R which is greater than 0.1 and less than 2.0, where R is defined as $(H_2-CO_2)/(CO+CO_2)$ based on molar concentrations of hydrogen and carbon oxides.

2. The method of claim 1 wherein the recycle ratio defined as the molar flow rate of said remaining portion of unreacted synthesis gas divided by the molar flow rate of said fresh synthesis gas feed is between about 0.1 and 2.0.

3. The method of claim 1 wherein said liquid phase reactor system is integrated with a coal gasification electric power generation system in which said fuel gas product is utilized to generate electric power and at least a portion of said methanol is stored and used as additional fuel to generate electric power during periods of peak electric power demand.

4. The method of claim 1 wherein said electric power is generated by one or more gas turbine-driven generators.

5. The method of claim 1, wherein said electric power is generated by one or more fuel cells.

6. The method of claim 1 wherein said methanol synthesis catalyst comprises copper.

7. The method of claim 1 wherein said liquid phase methanol reactor is operated in the pressure range of about 500 to 1500 psig.

8. The method of claim 1 wherein said liquid phase methanol reactor is operated in the temperature range of about 440° to 600° F.

9. The method of claim 1 wherein said liquid phase methanol reactor is operated in the temperature range of about 465° to 500° F.

* * * * *